US011892523B2

(12) United States Patent
Dempsey

(10) Patent No.: US 11,892,523 B2
(45) Date of Patent: Feb. 6, 2024

(54) MAGNETIC RESONANCE IMAGING

(71) Applicant: ViewRay Technologies, Inc., Mountain View, CA (US)

(72) Inventor: James F. Dempsey, Atherton, CA (US)

(73) Assignee: VIEWRAY TECHNOLOGIES, INC., Mountain View, CA (US)

( * ) Notice: Subject to any disclaimer, the term of this patent is extended or adjusted under 35 U.S.C. 154(b) by 0 days.

(21) Appl. No.: 17/848,277

(22) Filed: Jun. 23, 2022

(65) Prior Publication Data
US 2022/0334198 A1    Oct. 20, 2022

Related U.S. Application Data

(63) Continuation of application No. 15/630,890, filed on Jun. 22, 2017, now Pat. No. 11,378,629.
(Continued)

(51) Int. Cl.
| G01R 33/00 | (2006.01) |
| A61B 5/055 | (2006.01) |
| G01R 33/48 | (2006.01) |
| A61N 5/10 | (2006.01) |
| G01R 33/28 | (2006.01) |
| G01R 33/3815 | (2006.01) |

(Continued)

(52) U.S. Cl.
CPC .......... *G01R 33/0023* (2013.01); *A61B 5/055* (2013.01); *A61N 5/1049* (2013.01); *G01R 33/0017* (2013.01); *G01R 33/287* (2013.01); *G01R 33/385* (2013.01); *G01R 33/3815* (2013.01); *G01R 33/48* (2013.01); *A61N 2005/1055* (2013.01); *G01R 33/381* (2013.01);

*G01R 33/3806* (2013.01); *G01R 33/4808* (2013.01); *G01R 33/4835* (2013.01); *G01R 33/56325* (2013.01); *G01R 33/56527* (2013.01); *G01R 33/56536* (2013.01)

(58) Field of Classification Search
CPC .. A61B 5/055; G01R 33/0017; G01R 33/385; G01R 33/0023
See application file for complete search history.

(56) References Cited

U.S. PATENT DOCUMENTS

| 4,612,596 A | 9/1986 | Fox |
| 4,694,837 A | 9/1987 | Blakeley |

(Continued)

FOREIGN PATENT DOCUMENTS

| CN | 102472830 A | 5/2012 |
| CN | 102641561 A | 8/2012 |

(Continued)

OTHER PUBLICATIONS

Anixter Inc. World Headquarters; "Wire Wisdom"; 2014 NEC 310.106 (B); 1 Page; 2016.

(Continued)

*Primary Examiner* — Reena Aurora
(74) *Attorney, Agent, or Firm* — Pillsbury Winthrop Shaw Pittman LLP

(57) ABSTRACT

Improved magnetic resonance imaging systems, methods and software are described including a low field strength main magnet, a gradient coil assembly, an RF coil system, and a control system configured for the acquisition and processing of magnetic resonance imaging data from a patient while utilizing a sparse sampling imaging technique.

12 Claims, 3 Drawing Sheets

Related U.S. Application Data

(60) Provisional application No. 62/353,538, filed on Jun. 22, 2016.

(51) Int. Cl.
*G01R 33/385* (2006.01)
*G01R 33/381* (2006.01)
*G01R 33/565* (2006.01)
*G01R 33/483* (2006.01)
*G01R 33/38* (2006.01)
*G01R 33/563* (2006.01)

(56) References Cited

U.S. PATENT DOCUMENTS

| | | |
|---|---|---|
| 4,766,378 A | 8/1988 | Danby |
| 5,023,554 A | 6/1991 | Cho |
| 5,216,255 A | 6/1993 | Weidlich |
| 5,317,616 A | 5/1994 | Swerdloff |
| 5,332,908 A | 7/1994 | Weidlich |
| 5,351,280 A | 9/1994 | Swerdloff |
| 5,373,844 A | 12/1994 | Smith |
| 5,402,094 A | 3/1995 | Enge |
| 5,412,363 A | 5/1995 | Breneman |
| 5,442,675 A | 8/1995 | Swerdloff |
| 5,458,125 A | 10/1995 | Schweikard |
| 5,513,238 A | 4/1996 | Leber |
| 5,537,452 A | 7/1996 | Shepherd |
| 5,538,494 A | 7/1996 | Matsuda |
| 5,555,283 A | 9/1996 | Shiu |
| 5,570,022 A | 10/1996 | Ehnholm |
| 5,596,619 A | 1/1997 | Carol |
| 5,602,892 A | 2/1997 | Llacer |
| 5,602,982 A | 2/1997 | Llacer |
| 5,659,281 A | 8/1997 | Pissanetzky |
| 5,708,362 A | 1/1998 | Frese |
| 5,724,400 A | 3/1998 | Swerdloff |
| 5,734,384 A | 3/1998 | Yanof |
| 5,740,225 A | 4/1998 | Nabatame |
| 5,748,700 A | 5/1998 | Shepherd |
| 5,751,781 A | 5/1998 | Brown |
| 5,757,881 A | 5/1998 | Hughes |
| 5,802,136 A | 9/1998 | Carol |
| 5,815,547 A | 9/1998 | Shepherd |
| 5,851,182 A | 12/1998 | Sahadevan |
| 5,894,503 A | 4/1999 | Shepherd |
| 5,936,502 A | 8/1999 | Englund |
| 6,005,916 A | 12/1999 | Johnson |
| 6,011,393 A | 1/2000 | Kaufman |
| 6,038,283 A | 3/2000 | Carol |
| 6,052,430 A | 4/2000 | Siochi |
| 6,104,779 A | 8/2000 | Shepherd |
| 6,112,112 A | 8/2000 | Gilhuijs |
| 6,144,875 A | 11/2000 | Schweikard |
| 6,175,761 B1 | 1/2001 | Frandsen |
| 6,198,957 B1 | 3/2001 | Green |
| 6,223,067 B1 | 4/2001 | Vilsmeier |
| 6,240,162 B1 | 5/2001 | Hernandez-Guerra |
| 6,260,005 B1 | 7/2001 | Yang |
| 6,314,159 B1 | 11/2001 | Siochi |
| 6,320,377 B1 * | 11/2001 | Miyazaki ........... G01R 33/4838 324/309 |
| 6,330,300 B1 | 12/2001 | Siochi |
| 6,349,129 B1 | 2/2002 | Siochi |
| 6,366,798 B2 | 4/2002 | Green |
| 6,381,486 B1 | 4/2002 | Mistretta |
| 6,385,286 B1 | 5/2002 | Fitchard |
| 6,385,477 B1 | 5/2002 | Werner |
| 6,393,096 B1 | 5/2002 | Carol |
| 6,411,675 B1 | 6/2002 | Llacer |
| 6,414,487 B1 | 7/2002 | Anand |
| 6,414,490 B1 | 7/2002 | Damadian |
| 6,422,748 B1 | 7/2002 | Shepherd |
| 6,424,856 B1 | 7/2002 | Vilsmeier |
| 6,466,813 B1 | 10/2002 | Shukla |
| 6,487,435 B2 | 11/2002 | Mistretta |
| 6,504,899 B2 | 1/2003 | Pugachev |
| 6,512,813 B1 | 1/2003 | Krispel |
| 6,516,046 B1 | 2/2003 | Frohlich |
| 6,526,123 B2 | 2/2003 | Ein-Gal |
| 6,527,443 B1 | 3/2003 | Vilsmeier |
| 6,542,767 B1 | 4/2003 | McNichols |
| 6,546,073 B1 | 4/2003 | Lee |
| 6,560,311 B1 | 5/2003 | Shepard |
| 6,564,084 B2 | 5/2003 | Allred |
| 6,570,475 B1 | 5/2003 | Lvovsky |
| 6,584,174 B2 | 6/2003 | Schubert |
| 6,594,516 B1 | 7/2003 | Steckner |
| 6,600,810 B1 | 7/2003 | Hughes |
| 6,609,022 B2 | 8/2003 | Vilsmeier |
| 6,611,700 B1 | 8/2003 | Vilsmeier |
| 6,618,467 B1 | 9/2003 | Ruchala |
| 6,636,645 B1 | 10/2003 | Yu |
| 6,657,391 B2 | 12/2003 | Ding |
| 6,661,870 B2 | 12/2003 | Kapatoes |
| 6,708,054 B2 | 3/2004 | Shukla |
| 6,719,683 B2 | 4/2004 | Frohlich |
| 6,724,922 B1 | 4/2004 | Vilsmeier |
| 6,728,336 B2 | 4/2004 | Bortfeld |
| 6,731,970 B2 | 5/2004 | Schlossbauer |
| 6,735,277 B2 | 5/2004 | McNutt |
| 6,757,355 B1 | 6/2004 | Siochi |
| 6,772,002 B2 | 8/2004 | Schmidt |
| 6,778,850 B1 | 8/2004 | Adler |
| 6,792,074 B2 | 9/2004 | Erbel |
| 6,849,129 B2 | 2/2005 | Bilz et al. |
| 6,853,704 B2 | 2/2005 | Collins |
| 6,859,660 B2 | 2/2005 | Vilsmeier |
| 6,862,469 B2 | 3/2005 | Bucholz |
| 6,865,253 B2 | 3/2005 | Blumhofer |
| 6,865,411 B2 | 3/2005 | Erbel |
| 6,879,714 B2 | 4/2005 | Hutter |
| 6,885,886 B2 | 4/2005 | Bauch |
| 6,891,375 B2 | 5/2005 | Goto |
| 6,898,456 B2 | 5/2005 | Erbel |
| 6,915,005 B1 | 7/2005 | Ruchala |
| 6,937,696 B1 | 8/2005 | Mostafavi |
| 6,947,582 B1 | 9/2005 | Vilsmeier |
| 6,965,847 B2 | 11/2005 | Wessol |
| 6,980,679 B2 | 12/2005 | Jeung |
| 6,999,555 B2 | 2/2006 | Morf |
| 7,012,385 B1 | 3/2006 | Kulish |
| 7,046,762 B2 | 5/2006 | Lee |
| 7,046,765 B2 | 5/2006 | Wong |
| 7,046,831 B2 | 5/2006 | Ruchala |
| 7,050,845 B2 | 5/2006 | Vilsmeier |
| 7,092,573 B2 | 8/2006 | Luo |
| 7,095,823 B2 | 8/2006 | Topolnjak |
| 7,096,055 B1 | 8/2006 | Schweikard |
| 7,123,758 B2 | 10/2006 | Jeung |
| 7,130,372 B2 | 10/2006 | Kusch |
| 7,154,991 B2 | 12/2006 | Earnst |
| 7,162,005 B2 | 1/2007 | Bjorkholm |
| 7,166,852 B2 | 1/2007 | Saracen |
| 7,171,257 B2 | 1/2007 | Thomson |
| 7,180,366 B2 | 2/2007 | Roos |
| 7,191,100 B2 | 3/2007 | Mostafavi |
| 7,202,663 B2 | 4/2007 | Huang |
| 7,204,640 B2 | 4/2007 | Fu |
| 7,221,733 B1 | 5/2007 | Takai |
| 7,227,925 B1 | 6/2007 | Mansfield |
| 7,230,429 B1 | 6/2007 | Huang |
| 7,231,075 B2 | 6/2007 | Raghavan |
| 7,231,076 B2 | 6/2007 | Fu |
| 7,260,426 B2 | 8/2007 | Schweikard |
| 7,265,545 B2 | 9/2007 | Krueger |
| 7,266,175 B1 | 9/2007 | Romesberg |
| 7,266,176 B2 | 9/2007 | Allison |
| 7,289,599 B2 | 10/2007 | Seppi |
| 7,298,819 B2 | 11/2007 | Dooley |
| 7,302,038 B2 | 11/2007 | Mackie |
| 7,308,298 B2 * | 12/2007 | Miyazaki ............ G01R 33/563 324/309 |
| 7,315,636 B2 | 1/2008 | Kuduvalli |

(56) References Cited

U.S. PATENT DOCUMENTS

| | | |
|---|---|---|
| 7,317,782 B2 | 1/2008 | Bjorkholm |
| 7,318,805 B2 | 1/2008 | Schweikard |
| 7,324,626 B2 | 1/2008 | Vilsmeier |
| 7,327,865 B2 | 2/2008 | Fu |
| 7,366,278 B2 | 4/2008 | Fu |
| 7,394,081 B2 | 7/2008 | Okazaki |
| 7,403,638 B2 | 7/2008 | Jeung |
| 7,412,029 B2 | 8/2008 | Myles |
| 7,415,095 B2 | 8/2008 | Wofford |
| 7,417,434 B2 | 8/2008 | Overweg |
| 7,423,273 B2 | 9/2008 | Clayton |
| 7,426,318 B2 | 9/2008 | Fu |
| 7,444,178 B2 | 10/2008 | Goldbach |
| 7,460,637 B2 | 12/2008 | Clinthorne |
| 7,463,823 B2 | 12/2008 | Birkenbach |
| 7,471,813 B2 | 12/2008 | Ulmer |
| 7,477,776 B2 | 1/2009 | Lachner |
| 7,480,399 B2 | 1/2009 | Fu |
| 7,486,839 B2 | 2/2009 | Moriguchi |
| 7,505,037 B2 | 3/2009 | Wang |
| 7,505,617 B2 | 3/2009 | Fu |
| 7,522,779 B2 | 4/2009 | Fu |
| 7,532,705 B2 | 5/2009 | Yin |
| 7,542,622 B1 | 6/2009 | Angelini |
| 7,558,617 B2 | 7/2009 | Vilsmeier |
| 7,570,987 B2 | 8/2009 | Raabe |
| 7,577,474 B2 | 8/2009 | Vilsmeier |
| 7,589,326 B2 | 9/2009 | Mollov |
| 7,634,122 B2 | 12/2009 | Bertram |
| 7,636,417 B2 | 12/2009 | Bjorkholm |
| 7,638,752 B2 | 12/2009 | Partain |
| 7,657,304 B2 | 2/2010 | Mansfield |
| 7,659,718 B1 | 2/2010 | Lustig |
| 7,688,998 B2 | 3/2010 | Tuma |
| 7,728,311 B2 | 6/2010 | Gall |
| 7,741,624 B1 | 6/2010 | Sahadevan |
| 7,785,358 B2 | 8/2010 | Lach |
| 7,791,338 B2 | 9/2010 | Kim |
| 7,840,045 B2 | 11/2010 | Guo |
| 7,902,530 B1 | 3/2011 | Sahadevan |
| 7,907,987 B2 | 3/2011 | Dempsey |
| 7,957,507 B2 | 6/2011 | Cadman |
| 8,139,714 B1 | 3/2012 | Sahadevan |
| 8,155,417 B2 | 4/2012 | Piron |
| 8,190,233 B2 | 5/2012 | Dempsey |
| 8,214,010 B2 | 7/2012 | Courtney |
| 8,310,233 B2 | 11/2012 | Trzasko |
| 8,331,531 B2 | 12/2012 | Fahrig |
| 8,405,395 B2 * | 3/2013 | Setsompop ........ G01R 33/4835 324/309 |
| 8,460,195 B2 | 6/2013 | Courtney |
| 8,803,524 B2 | 8/2014 | Dempsey |
| 8,836,332 B2 | 9/2014 | Shvartsman |
| 8,983,573 B2 | 3/2015 | Carlone |
| 9,114,253 B2 | 8/2015 | Dempsey |
| 9,289,626 B2 | 3/2016 | Kawrakow |
| 9,421,398 B2 | 8/2016 | Shvartsman |
| 9,423,477 B2 | 8/2016 | Dempsey |
| 9,446,263 B2 | 9/2016 | Dempsey |
| 9,472,000 B2 | 10/2016 | Dempsey |
| 9,526,918 B2 | 12/2016 | Kruip |
| 9,638,773 B2 | 5/2017 | Poole |
| 10,026,186 B2 | 7/2018 | Gerganov |
| 10,613,171 B2 * | 4/2020 | Li ...................... G01R 33/5605 |
| 10,650,532 B2 | 5/2020 | Gerganov |
| 11,209,509 B2 | 12/2021 | Dempsey |
| 11,378,629 B2 * | 7/2022 | Dempsey ............. G01R 33/287 |
| 2001/0001807 A1 | 5/2001 | Green |
| 2001/0049475 A1 | 12/2001 | Bucholz |
| 2002/0046010 A1 | 4/2002 | Wessol |
| 2002/0091315 A1 | 7/2002 | Spetz |
| 2002/0150207 A1 | 10/2002 | Kapatoes |
| 2003/0068097 A1 | 4/2003 | Wilson |
| 2003/0155530 A1 | 8/2003 | Adnani |
| 2003/0181804 A1 | 9/2003 | Gagnon |
| 2003/0219098 A1 | 11/2003 | McNutt |
| 2004/0054248 A1 | 3/2004 | Kimchy |
| 2004/0254448 A1 | 12/2004 | Amies |
| 2004/0254773 A1 | 12/2004 | Zhang |
| 2005/0053267 A1 | 3/2005 | Mostafavi |
| 2005/0054916 A1 | 3/2005 | Mostafavi |
| 2005/0143965 A1 | 6/2005 | Failla |
| 2005/0197564 A1 | 9/2005 | Dempsey |
| 2005/0201516 A1 | 9/2005 | Ruchala |
| 2005/0207531 A1 | 9/2005 | Dempsey |
| 2005/0254623 A1 | 11/2005 | Kamath |
| 2005/0264578 A1 | 12/2005 | Engel |
| 2006/0033496 A1 | 2/2006 | Shvartsman |
| 2006/0058636 A1 | 3/2006 | Wemple |
| 2006/0074292 A1 | 4/2006 | Thomson |
| 2006/0079754 A1 | 4/2006 | Welch |
| 2006/0100502 A1 | 5/2006 | Chen |
| 2006/0120583 A1 | 6/2006 | Dewaele |
| 2006/0193441 A1 | 8/2006 | Cadman |
| 2007/0003021 A1 | 1/2007 | Guertin |
| 2007/0016014 A1 | 1/2007 | Hara |
| 2007/0083114 A1 | 4/2007 | Yang |
| 2007/0110159 A1 | 5/2007 | Wang |
| 2007/0159174 A1 | 7/2007 | Oshio |
| 2007/0197908 A1 | 8/2007 | Ruchala |
| 2007/0216409 A1 | 9/2007 | Overweg |
| 2007/0230770 A1 | 10/2007 | Kulkarni |
| 2007/0244386 A1 | 10/2007 | Steckner |
| 2008/0049896 A1 | 2/2008 | Kuduvalli |
| 2008/0093567 A1 | 4/2008 | Gall |
| 2008/0177138 A1 | 7/2008 | Courtney |
| 2008/0197842 A1 | 8/2008 | Lustig |
| 2008/0208036 A1 | 8/2008 | Amies |
| 2008/0303457 A1 | 12/2008 | Maltz |
| 2009/0003532 A1 | 1/2009 | Weber |
| 2009/0039886 A1 | 2/2009 | White |
| 2009/0066727 A1 | 3/2009 | Lu |
| 2009/0129545 A1 | 5/2009 | Adler |
| 2009/0149735 A1 | 6/2009 | Fallone |
| 2009/0175418 A1 | 7/2009 | Sakurai |
| 2009/0240135 A1 | 9/2009 | Gleich |
| 2009/0264768 A1 | 10/2009 | Courtney |
| 2010/0008097 A1 | 1/2010 | Illium |
| 2010/0033186 A1 | 2/2010 | Overweg |
| 2010/0113911 A1 | 5/2010 | Dempsey |
| 2010/0239066 A1 | 9/2010 | Fahrig |
| 2010/0303358 A1 | 12/2010 | Acharyya |
| 2010/0304976 A1 | 12/2010 | Overweg |
| 2010/0312100 A1 | 12/2010 | Zarkh |
| 2010/0322497 A1 | 12/2010 | Dempsey |
| 2011/0012593 A1 | 1/2011 | Shvartsman |
| 2011/0051893 A1 | 3/2011 | McNutt |
| 2011/0087090 A1 | 4/2011 | Boernert |
| 2011/0118588 A1 | 5/2011 | Komblau |
| 2011/0121832 A1 | 5/2011 | Shvartsman |
| 2011/0156703 A1 | 6/2011 | O'Connor |
| 2011/0218420 A1 | 9/2011 | Carlone |
| 2011/0241684 A1 | 10/2011 | Dempsey |
| 2011/0284757 A1 | 11/2011 | Butuceanu |
| 2011/0285960 A1 | 11/2011 | Kohn |
| 2012/0022363 A1 | 1/2012 | Dempsey |
| 2012/0114208 A1 | 5/2012 | Hirasawa |
| 2012/0150017 A1 | 6/2012 | Yamaya |
| 2012/0155727 A1 | 6/2012 | Orderud |
| 2012/0165652 A1 | 6/2012 | Dempsey |
| 2012/0177260 A1 | 7/2012 | Su |
| 2012/0197102 A1 | 8/2012 | Hanebuchi |
| 2012/0245453 A1 | 9/2012 | Tryggestad |
| 2012/0253172 A1 | 10/2012 | Loeffler |
| 2012/0320055 A1 | 12/2012 | Pekar |
| 2013/0066135 A1 | 3/2013 | Rosa |
| 2013/0141094 A1 | 6/2013 | Miyazaki |
| 2013/0147476 A1 | 6/2013 | Shvartsman |
| 2013/0195335 A1 | 8/2013 | Gorman |
| 2013/0223711 A1 | 8/2013 | Knapp |
| 2013/0261429 A1 | 10/2013 | Lee |
| 2013/0261430 A1 | 10/2013 | Uhlemann |
| 2013/0345545 A1 | 12/2013 | Gross |
| 2013/0345556 A1 | 12/2013 | Courtney |

(56) References Cited

U.S. PATENT DOCUMENTS

| | | |
|---|---|---|
| 2014/0003023 A1 | 1/2014 | Weibler |
| 2014/0003691 A1 | 1/2014 | Serlie |
| 2014/0084926 A1 | 3/2014 | Amthor |
| 2014/0112453 A1 | 4/2014 | Prince |
| 2014/0128719 A1 | 5/2014 | Longfield |
| 2014/0135615 A1 | 5/2014 | Krulp |
| 2014/0266208 A1 | 9/2014 | Dempsey |
| 2014/0275963 A1 | 9/2014 | Shvartsman |
| 2014/0343543 A1 | 11/2014 | Karnik |
| 2014/0347053 A1 | 11/2014 | Dempsey |
| 2015/0065860 A1 | 3/2015 | Shvartsman |
| 2015/0087881 A1 | 3/2015 | Miyamoto |
| 2015/0126850 A1 | 5/2015 | Cetingul |
| 2015/0302601 A1 | 10/2015 | Rivet-Sabourin |
| 2015/0346304 A1 | 12/2015 | Hu |
| 2016/0232690 A1 | 8/2016 | Ahmad |
| 2016/0252596 A1 | 9/2016 | Nielsen |
| 2016/0256712 A1 | 9/2016 | Vahala |
| 2016/0324500 A1 | 11/2016 | Fan |
| 2016/0324664 A1 | 11/2016 | Piron |
| 2016/0334479 A1 | 11/2016 | Poole |
| 2016/0356869 A1 | 12/2016 | Dempsey |
| 2017/0001039 A1 | 1/2017 | Dempsey |
| 2017/0014644 A1 | 1/2017 | Shvartsman |
| 2017/0032544 A1 | 2/2017 | Dempsey |
| 2017/0371001 A1 | 12/2017 | Dempsey |
| 2018/0143274 A1 | 5/2018 | Poole |
| 2019/0168028 A1 | 6/2019 | Dempsey |
| 2019/0217126 A1 | 7/2019 | Shvartsman |
| 2019/0353724 A1 | 11/2019 | Snelten |
| 2019/0353725 A1 | 11/2019 | Dempsey |
| 2020/0086143 A1 | 3/2020 | Maltz |
| 2020/0147412 A1 | 5/2020 | Ni |
| 2020/0246637 A1 | 8/2020 | Wang |

FOREIGN PATENT DOCUMENTS

| | | |
|---|---|---|
| EP | 1761794 | 3/2007 |
| EP | 2359905 A1 | 8/2011 |
| FR | 2839894 A1 | 11/2003 |
| GB | 2219406 | 12/1989 |
| GB | 2393373 A | 3/2004 |
| JP | 2001517132 A | 10/2001 |
| JP | 2002186676 A | 7/2002 |
| JP | 2002522129 A | 7/2002 |
| JP | 2004509723 | 4/2004 |
| JP | 2005103295 A | 4/2005 |
| JP | 2006218315 | 8/2006 |
| JP | 2007526036 A | 9/2007 |
| JP | 2009501043 A | 1/2009 |
| JP | 2009511222 A | 3/2009 |
| JP | 2009160309 A | 7/2009 |
| JP | 2009160378 | 7/2009 |
| JP | 2011041656 | 3/2011 |
| JP | 2012029767 | 2/2012 |
| JP | 2013190421 | 9/2013 |
| JP | 2014502541 | 2/2014 |
| JP | 2015511139 | 4/2015 |
| JP | 2016513560 | 5/2016 |
| JP | 2016516508 | 6/2016 |
| WO | 1999032189 | 7/1999 |
| WO | 2002072190 A2 | 9/2002 |
| WO | 20030008986 | 1/2003 |
| WO | 2004024235 A1 | 3/2004 |
| WO | 2005081842 A2 | 9/2005 |
| WO | 2006007277 A2 | 1/2006 |
| WO | 2006097274 A1 | 9/2006 |
| WO | 2007007276 A2 | 1/2007 |
| WO | 2007014105 A2 | 2/2007 |
| WO | 2007045076 A1 | 4/2007 |
| WO | 2008013598 A2 | 1/2008 |
| WO | 2009099001 | 8/2009 |
| WO | 2009155700 A1 | 12/2009 |
| WO | 2010103644 A1 | 9/2010 |
| WO | 2010143400 | 12/2010 |
| WO | 2011008969 A1 | 1/2011 |
| WO | 2012164527 A1 | 12/2012 |
| WO | 2015138941 | 9/2015 |
| WO | 2015138945 | 9/2015 |
| WO | WO-2015138945 A1 * | 9/2015 ........... G01R 33/445 |

OTHER PUBLICATIONS

AU Search Report dated Dec. 11, 2017; 2 pages.

Aytekin OTO, MD, et al., Multidetector Row CT of the Liver; (2005) 43 ERDCNA 5 827-848.

B W Raaymakers et al.; "Integrating a 1.5 T MRI Scanner with a 6 MV Accelerator: Proof of Concepts," Physics in Medicine and Biology. vol. 54, No. 12, May 19, 2009, pp. N229-N237, XP055395399, Bristol GB ISSN: 0031-9155. 9 pages.

Balter, James M., et al. 'Accuracy of a Wireless Localization System for Radiotherapy' Int. J. Radiation Oncology Biol. Phys., vol. 61, No. 3. pp. 933-937, Nov. 1, 2004, Elsevier Inc., USA.

Baro, J et al. 'Penelope: An algorithm for Monte Carlo simulation of the penetration and energy loss of electrons and positrons in matter' Nuclear Instruments and Methods in Physics Research B 100 (1995) 31-46, Elsevier Science B.V.

Barth, et al. "Simultaneous Multislice (SMS) Imaging Techniques." Magnetic Resonance in Medicine; vol. 75; pp. 63-81; 2016.

Bernier, Jacques et al. 'Radiation oncology: a century of achievements' Nature Reviews-Cancer, vol. 4, Sep. 2004. pp. 737-747.

Bhat et al. "3D Radial Sampling and 3D Affine Transform-based Respiratory Motion Correction Technique for Free-breathing Whole-Heart Coronary MRA with 100% Imaging Efficiency". Magn Reson Med. May 2011 ; 65(5): 1269-1277. doi:10.1002/mrm .22717. (Year: 2011).

Bilgin, A. et al. 'Randomly Perturbed Radial Trajectories for Compressed Sensing MRI.' Proceedings of International Society for Magnetic Resonance in Medicine 16 (2008):p. 3152.

Blaimer, et al. 'Smash, Sense, Pills, Grappa, How to Choose the Optimal Method'. Top Magan Reson Imaging, vol. 15, No. 4, Aug. 2004, pp. 223-236.

Buchanan, Roger 'Cobalt on the way out' British Medical Journal, vol. 292, Feb. 1, 1986. p. 290.

Buerger et al. "3D Non-Rigid Motion Modeling of the Liver from Undersampled Golden-Radial Phase Encoding (G-RPE) Acquisitions". Proc. Intl. Soc. Mag. Reson. Med. 19 (2011). p. 643. (Year: 2011).

Candes, et al. 'Robust Uncertainty Principles: Exact Signal Reconstruction from Highly Incomplete Frequency Information.' IEEE Transactions on Information Theory, vol. 52, No. 2, Feb. 2006, pp. 489-509.

Candes, et al. 'Sparsity and Incoherence in Compressive Sampling'. Electrical and Computer Engineering, Georgia Tech, Atlanta, GA, 90332. Nov. 2006, pp. 1-20.

Chng, N. et al. 'Development of inverse planning and limited angle CT reconstruction for cobalt-60 tomotherapy' Proceedings of 51st Annual Meeting of Canadian Organization of Medical Physicists and the Canadian College of Physicists in Medicine, 2005, McMaster University, Hamilton Ontario. Medical Physics, 2005, p. 2426. (4 pages).

CIPRA 'L1-magic' from SIAM News, vol. 39, No. 9, Nov. 2006. (3 pages).

Cosmus, Thomas C. et al.; "Advances in Whole-Body MRI Magnets"; IEEE/CSC & ESAS European Superconductivity New Forum (ESNF), No. 14; Oct. 2010; 6 Pages; The published version of this manuscript appeared in IEEE Transactions on Applied Superconductivity 21, Issue 3; pp. 2104-2109 (2011).

Crijns et al. "Proof of concept of MRI-guided tracked radiation delivery: tracking one-dimensional motion". Phys. Med. Biol. 57 (2012 ) 7863-7872 doi: 10.1088/0031-9155/57/23/7863 (Year: 2012).

De Poorter J. et al. 'Noninvasive MRI Thermometry with the Proton Resonance Frequencey (PRF) Method: In Vivo Results in Human Muscle,' Magnetic Resonance in Medicine, Academic Press, Duluth, vol. 33, No. 1, Jan. 1995 pp. 74-81 XP000482971.

Donoho, David L., 'Compressed Sensing'. Department of Statistics, Stanford University. Sep. 14, 2004. (34 pages).

(56) References Cited

OTHER PUBLICATIONS

EP App. No. 10195476.6; Extended EP Search Report dated Jul. 4, 2011; 11 pages.

EP App. No. 17000760.3; Extended EP Search Report dated Nov. 9, 2017; 7 pages.

EU Office Action in app. 17734947.9, dated Oct. 14, 2021.

Fofanov, Dr. Denis et al.; "Magentic Properties of Stainless Steels: Applications, Opportunities and New Developments"; https://steelmehdipour.net/wp-content/uploads/2017/02/Magnetic-properties-of-stainless-steels.pdf ; Webpage retrieved Feb. 2017; 13 Pages.

Foroosh, Hassan, et.al. 'Extension of Phase Correlation to Subpixel Registration.' IEEE Transactions on Image Processing, vol. 11, No. 3, 2002, pp. 188-200.

Gerganov G et al, 'Portal image registration using the phase correlation method', 2013 IEEE Nuclear Science Symposium and Medical Imaging Conference (2013 NSS/MIC), IEEE, (Oct. 27, 2013), doi:10.1109/NSSMIC.2013.6829306, pp. 1-3, XP032601397.

Goitein, Michael. 'Organ and Tumor Motion: An Overview.' Seminars in Radiation Oncology. vol. 14, No. 1 Jan. 2004: pp. 2-9.

Goldberg, S. Nahum; G. Scott Gazelle, and Peter R. Mueller. 'Thermal Ablation Therapy for Focal Malignancy: A Unified Approach to Underlying Principles, Techniques, and Diagnostic Imaging Guidance.' Amer. J. of Roentgenology, vol. 174, Feb. 2000 pp. 323-331 XP002431995.

Haacke, Mark E. et al. 'Constrained reconstruction: A superresolution, optimal signal-to-noise alternative to the Fourier transform in magnetic resonance imaging.' Medical Physics, AIP, Melville, NY, US, vol. 16, No. 3, May 1, 1989 (May 1, 1989), pp. 388-397, XP000034068, ISSN: 0094-2405, DDI: 10.1118/1.596427.

Hajdok, George. 'An Investigation of Megavoltage Computed Tomography Using a Radioactive Cobalt-60 Gamma Ray Source for Radiation Therapy Treatment Verification.' Thesis. May 2002. 150 pages.

Hernando, D. et al. 'Interventional MRI with sparse sampling: an application of compressed sensing.' Proceedings of International Society for Magnetic Resonance in Medicine. 16 (2008):p. 1482.

Hong Pan, et al., Review; New and Emerging Techniques for Mapping Brain Circuitry; (2011) 67 ESBRR 1-2 226-251.

International Preliminary Report on Patentability, International Applicaiton No. PCT/US2018/059245, International Filing Date Nov. 5, 2018, dated Nov. 26, 2020, 24 pages.

International Search Report of the International Searching Authority issued in International Application No. PCT/US2014/028792, dated Jul. 2, 2014. 3 pages.

Irarrazabal, Pablo, and Dwight G. Nishimura. 'Fast Three Dimensional Magnetic Resonance Imaging.' Magnetic Resonance in Medicine, vol. 33, No. 5, 1995, pp. 656-662.

Jaffray, David A., et al. 'Flat-Panel Cone Beam Computed Tomography for Image-Guided Radiation Therapy' Int. J. Radiation Oncology Biol. Phys., vol. 53, No. 5, pp. 1337-1349, Apr. 3, 2002, Elsevier Science Inc., USA.

Jan J. W. Lagendijk et al.; "MR Guidance in Radiotherapy", Physics in Medicine and Biology, Institute of Physics Publishing, Bristol GB, vol. 59, No. 21, Oct. 16, 2014, pp. R349-R369, XP020272054, ISSN: 0031-9155.

Japanese Office Action, Application No. 2018-567084, dated Mar. 30, 2021 (pp. 1-6).

JP Office Action dated Jan. 11, 2022, Japanese Patent Application No. 2018-567083.

Jursinic, Paul et al. 'Characteristics of secondary electrons produced by 6, 10 and 24 MV x-ray beams' Phys. Med. Biol. 41 (1996) 1499-1509, United Kingdom.

Khan, Faiz M., 'The Physics of Radiation Therapy (second edition)', Lippincott Williams & Wilkins. Chapter 13. 1985. pp. 323-332.

Kim et al. "Extraction of Cardiac and Respiratory Motion Cycles by Use of Projection Data and Its Applications to NMR Imaging". Magnetic Resonance in Medicine 13,25-37 (1990). (Year: 1990).

Kolbitsch, C. et al; "Cardiac Function Asssesment Without ECG Using Image-based Navigation"; Proceeding of the International Society for Magnetic Resonance in Medincine, 20th Annual Meeting & Exhibition; May 5, 2010; p. 3849; KP040626270; Maelbourne, Australia.

Kolbitsch, C. et al; "Image-based Self-navigator Using Cardiac Functional Parameters for Cine Imaging"; Proceeding of the International Society for Magnetic Resonance in Medincine, 20th Annual Meeting & Exhibition; May 5, 2010; p. 602; KP040623030; Maelbourne, Australia.

Krombach G.A. "MRI Guidance of Vascular Applications". In: Kahn T., Busse H. (eds) Interventional Magnetic Resonance Imaging. Medical Radiology. Springer, Berlin, Heidelberg. (2011) (Year: 2011), 31 pages.

Kwan-Jin Jung, et al., "Parallel Imaging with Asymmetric Acceleration to Reduce Gibbs Artifacts and to Increase Signal-To-Noise Ratio of the Gradient Echo Echo-Planar Imaging Sequence for Functional MRI," Magnetic Resonance in Medicine 67:419-427 (2012).

Lagendijk et al., 'MRI/linac integration', Radiotherapy and Oncology, Elsevier, Ireland, (Nov. 26, 2007), vol. 86, No. 1, doi:10.1016/J.RADONC.2007.10.034, ISSN 0167-8140, pp. 25-29, XP022423061.

Lagendijk JJ W et al.: "MRI Guided Radiotherapy: A MRI based linear Accelerator", Radiotherapy and Oncology, vol. 56, No. 01, Sep. 21, 2000 (Sep. 21, 2000), pp. S60-S61.

Langen, K.M. et al. 'Organ Motion and its Management.' Int J. Radiation Oncology Biol. Phys., vol. 50, No. 1, pp. 265-278. 2001. Elsevier Science Inc., USA.

Yang, Junfeng, et al. 'A Fast TVL1-L2 Minimization Algorithm for Signal Reconstruction from Rartial Fourier Data.' Technical Report, TR08-27, CAAM, Rice University Houston, TX, 2008. pp.1-10.

Yoon et al. "Accuracy of an Automatic Patient-Positioning System Based on the Correlation of Two Edge Images in Radiotherapy", Journal of Digital Imaging, vol. 24, No. 2 (Apr. 2011: pp. 322-330).

Yuichiro Tajima, et al., "A Study on Non-Rigid vol. Registration Using 3D Phase-Only Correlation," Technical Report of the Institute of Electronics, Information and Communication Engineers, Japan, IEICE, May 10, 2012, vol. 112, No. 38, pp. 107-112.

Zaitsev M et al.: "Shared k-space Echo Planar Imaging with Keyhole," Magnetic Resonance in Medicine, John Wiley & Sons, Inc. US, vol. 45, Jan. 1, 2001, pp. 109-117, XP002311925, ISSN: 0740-3194.

Zitova B et al, 'Image Registration Methods: A Survey', Image and Vision Computing, Elsevier, Guildford, GB, (Oct. 1, 2003), vol. 21, No. 11, doi:10.1016/S0262-8856(03)00137-9, ISSN 0262-8856, pp. 977-1000, XP001189327.

Law, C. , and Glover, G. 'Deconvolving Haemodynamic Response Function in fMRI under high noise by Compressive Sampling.' Proceedings of International Society for Magnetic Resonance in Medicine. 17 (2009):p. 1712. Stanford University, Stanford, CA, United States.

Li, Kang and Kanadae, Takeo. 'Nonnegative Mixed-Norm Preconditioning for Microscopy Image Segmentation.' Information Processing in Medical Imaging. Springer Berlin Heidelberg. vol. 5636. (2009):362-373.

Liang, J. and D. Yan. 'Reducing Uncertainties in Volumetric Image Based Deformable Organ Registration.' Medical Physics, vol. 30, No. 8, 2003, pp. 2116-2122.

Lin et al. "Heart deformation analysis: measuring regional myocardial velocity with MR imaging". Int J Cardiovasc Imaging (2016) 32 :1103-1111. DOI 10.1007/s10554-016-0879-z (Year: 2016).

Lopez, Hector Sanchez et al.; "Designing an Efficient Resistive Magnet for Magnetic Resonance Imaging"; IEEE Transactions on Magnetics, vol. 40, No. 5; Sep. 2004; pp. 3378-3381.

Lopez, Mike R. et al. 'Relativistic Magnetron Driven by a Microsecond E-Beam Accelerator with a Ceramic Insulator' IEEE Transactions on Plasma Science vol. 32, No. 3, Jun. 2004. pp. 1171-1180.

Lurie, D.J., PhD. 'Free radical imaging' The British Journal of Radiology. 74 (2001). pp. 782-784.

Lustig, et al. 'L1 SPIR-IT: Autocalibrating Parallel Imaging Compressed Sensing.' Electrical Engineering, Stanford University, Stanford, CA, United States. Radiology, Stanford University. Statistics, Stanford University (p. 334).

(56) References Cited

OTHER PUBLICATIONS

Lustig, M, et al. 'Faster Imaging with Randomly Perturbed, Undersampled Spirals and |L|_1 Reconstruction.' In: Proceedings of the 13th Annual Meeting of ISMRM, Miami Beach, 2005. (1 page).

Lustig, M, et. al. "L1 SPIR-iT: Autocalibrating Parallel Imaging Compressed Sensing." In: Proceedings of the Seventeenth Meeting of the International Society for Magnetic Resonance in Medicine. Berkeley, Calif: International Society for Magnetic Resonance in Medicine, 2009 p. 334.

Mah et al., "Measurement of intrafractional prostate motion using magnetic resonance imaging, " Int. J. Radiation Oncology Boil. Phys. Vo.54, No. 2, pp. 568-575, 2002.

Mathieu Sarracanie et al: "Low Cost High Performance MRI", Proceedings of the International Society for Magnetic Resonance in Medicine, vol. 23, 702, May 15, 2015.

Meulenbroeks, David; "Aluminum versus Copper Conductors—Application of Aluminum Conductors in Bus Way Systems for more Sustainable Data Centers" ; Siemens Center of Competence Data Centers , The Netherlands; www.siemens.com/datacenter, White Paper Oct. 2014; 9 Pages.

Meyer, et al. "Fast Spiral Coronary Artery Imaging", Magnetic Resonance in Medicine 28, pp. 202-213 (1992).

Momy, A. et al.; "Low-Leakage Wide-Access Magnet for MRI"; IEEE Transactions on Magnetics, vol. 33, No. 6; Nov. 1997; pp. 4572-4574.

Morgan, Patrick N. et al.; "Resistive Homogeneous MRI Magnet Design by Matrix Subset Selection"; Magnetic Resonance in Medicine 41:1221-1229; Wiley-Liss, Inc. (1999).

Mutic Sasa et al: "The ViewRay System: Magnetic Resonance-Guided and Controlled Radiotherapy", Seminars in Radiation Oncology, vol. 24, No. 3, Jun. 12, 2014 (Jun. 12, 2014), pp. 196-199.

Noel C et al: "TU-G-217A-09: Feasibility of Bowel Tracking Using Onboard Cine MRI for Gated Radiotherapy", Medical Physics, Jun. 28, 2012 (Jun. 28, 2012), pp. 1-2, XP55832625, Retrieved from the Internet: URL:https://aapm.onlinelibrary.wiley.com/doi/abs/10.1118/1.

Overweg et al. 'System for MRI guided Radiotherapy.' Proc. Intl. Soc. Mag. Reson. Med. 17(2009):594.

Overweg, Johan; " MRI Main Field Magnets"; Philips Research; Hamburg, Germany; 7 Pages.

Paganelli Chiara et al; Liver 4DMRI: A Retrospective Image-based Sorting Method, Medical Physics, AIP; Melville, NY, US; vol. 42; No. 8; Jul. 24, 2015; pp. 4814-4821; XP012199252; ISSN: 0094-2405; DOI: 10.1118/1.4927252 (Retrieved on Jan. 1, 1901); Section 2.B.

PCT App. No. PCT/US2010/039036; International Search Report dated Aug. 11, 2010. (pp. 1-2).

PCT App. No. PCT/US2017/038520; International Preliminary Report on Patentability dated Jan. 3, 2019. (pp. 1-10).

PCT App. No. PCT/US2017/038520; International Search Report and Written Opinion dated Oct. 4, 2017. (pp. 1-16).

PCT App. No. PCT/US2017/038867; International Search Report and Written Opinion dated Nov. 8, 2017. (pp. 1-12).

Pryor, Larry et a.: "A Comparison of Aluminum vs. Copper Used in Electrical Equipment"; 7 Pages.

Raaijmakers, A.J.E. et al. 'Integrating a MRI scanner with a 6 MV radiotherapy accelerator: dose increase at tissue-air interfaces in a lateral magnetic field due to returning electrons.' Phys. Med. Biol. 50 (2005) pp. 1363-1376.

Raaymakers, B.W. et al. 'Integrating a MRI scanner with a 6 MV radiotherapy accelerator: dose deposition in a transverse magnetic field', Phys. Med. Biol. 49 (2004) 4109-4118.

Reddy, B. Srinivasa, and B. N. Chatterji. 'An FFT-Based Technique for Translation, Rotation, and Scale-Invariant Image Registration.' IEEE Transactions on Image Processing, vol. 5, No. 8, Aug. 1996, pp. 1266-1271.

Riek, et al. "Flow Compensation in MRI Using a Phase-Corrected Real Reconstruction", Magnetic Resonance in Medicine 30, pp. 724-731, 1993.

Riek, Jonathan K, et al. 'Flow Compensation in MRI Using a Phase-Corrected Real Reconstruction.' Magnetic Resonance in Medicine, vol. 30, No. 6, 1993, pp. 724-731.

Roullot Elodie et al. 'Regularized reconstruction of 3D high-resolution magnetic resonance images from acquisitions of anisotropically degraded resolutions.' Pattern Recognition, 2000. Proceedings. 15th International Conference on Sep. 3-7, 2000; [Proceedings of the International Conference on Pattern Recognition. (ICPR)], Los Alamitos, CA, USA, IEEE Comput. Soc, US, vol. 3, Sep. 3, 2000 (Sep. 3, 2000), pp. 346-349.

Sanchez, H. et al.; "Approach to Design an Efficient Resistive Magnet for MRI"; Proc. Intl. Soc. Mag, Reson. Med. 11 (2003); p. 2409.

Schreiner, John; Kerr, Andrew; Salomons, Greg; Dyck, Christine, and Hajdok, George, 'The Potential for Image Guided Radiation Therapy with Cobalt-60 Tomotherapy', MICCAI 2003, LNCS 2879, pp. 449-456, 2003.

Schreiner, L. John, et al. 'The role of Cobalt-60 in modern radiation therapy: Dose delivery and image guidance'. Journal of Medical Physics, vol. 34, No. 3, 2009, 133-136.

Sempau, Josep et al. 'DPM, a fast, accurate Monte Carlo code optimized for photon and electron radiotherapy treatment planning dose calculations.' Phys. Med. Biol. 45 (2000) pp. 2263-2291, Printed in the UK.

Sherouse, George W. et al. 'Virtual Simulation in the Clinical Setting: Some Practical Considerations', Int. J. Radiation Oncology Biol. Phys. vol. 19, pp. 1059-1065, Apr. 26, 1990, Pergamon Press, USA.

Smolikova, R. et al.; "Registration of Fast Cine Cardiac MR Slices to 3D Procedural Images: Toward Real Time Registration for MRI-guided Procedures"; Proceedings of SPIE, Medical Imaging 2004; vol. 5370 II; Feb. 16, 2004; pp. 1195-1205; XP040181910; San Diego, CA.

St. Aubin et al,, 'Magnetic decoupling on the linac in a low field biplanar linac-MR system', Med. Phys, 37 (9), Sep. 2010, pp. 4755-4761.

Tamada and Kose. 'Two-Dimensional Compressed Sensing Using the Cross-sampling Approach for Low-Field MRI Systems.' IEEE Transactions on Medical Imaging. vol. 33, No. 9. Sep. 2014. pp. 1905-1912.

Tokuda, Junichi; Morikawa, Shigehiro; Dohi, Takeyoshi; Hata, Nobuhiko; Motion Tracking in MR-Guided Liver Therapy by Using Navigator Echoes and Projection Profile Matching, 2004. vol. 11. No. 1. pp. 111-120.

Trzasko et al. 'Highly Undersampled Magnetic Resonance Image Reconstruction via Homotopic L0—Minimization' IEEE Transactions on Medical Imaging. vol 28. No. 1. Jan. 31, 2009, pp. 106-121.

Trzasko et al. (Highly Undersampled Magnetic Resonance Image Reconstruction vai Homotopic L0-Minimization, IEEE Transactions on Medical Imaging, Jul. 2, 2008, pp. 1-16). Article previously submitted by Applicant via IDS.

Von Siebenthal et al., "4D MR imaging of respiratory organ motion and its variability". Physics in Medicine and Biology, pp. 1547 1564, Mar. 31, 2007.

Von, Siebenthal M. et al; "4D MR Imaging of Respiratory Organ Motion and its Variability; 4D MRI of Respiratory Organ Motion", Physics in Medicine and Biology, Institute of Physics Publishing, Bristol GB, vol. 52, No. 6, Mar. 21, 2007, pp. 1547-1564, XP20113239, ISSN: 0031-9155, DOI: 10.1088/0031-9155/52/6/001, pp. 1547-1553.

Warrington, Jim et al. 'Cobalt 60 Teletherapy for Cancer: A Revived Treatment Modality for the 21st Century', 2002 The Institution of Electrical Engineers, pp. 19-1-19/19.

Wazer, David E. et al. 'Principles and Practice of Radiation Oncology (fifth edition).', Wolters Kluwer/Lippincott Williams & Wilkins. 2008. 2 pages.

Weaver, John B.; "Simultaneous Multislice Acquisition of MR Images", Magnetic Resonance in Medicine, John Wiley & Sons, Inc., vol. 8, No. 3, Nov. 1, 1988, pp. 275-284, XP000003030, ISSN: 0740-3194.

Webb, S. 'The physical basis of IMRT and inverse planning' The British Journal of Radiology, 76 (2003), 678-689, 2003 The British Institute of Radiology.

(56) References Cited

OTHER PUBLICATIONS

Webb, Steve, 'Intensity-modulated radiation therapy using only jaws and a mask: II. A simplified concept of relocatable single-bixel attenuators', published May 22, 2002, Institute of Physics Publishing, Physics in Medicine and Biology, Phys. Med. Biol. 47 (2002) 1869-1879.

* cited by examiner

MAGNETIC RESONANCE IMAGING

CROSS-REFERENCE TO RELATED APPLICATION

This application is a continuation of U.S. patent application Ser. No. 15/630,890, filed Jun. 22, 2017, entitled "MAGNETIC RESONANCE IMAGING," which claims the benefit of priority under 35 U.S.C. 119 of U.S. Provisional Application No. 62/353,538, filed Jun. 22, 2016, entitled "MAGNETIC RESONANCE IMAGING," the disclosures of each are incorporated herein by reference in their entirety.

TECHNICAL FIELD

The subject matter described herein relates to systems, methods and computer software for magnetic resonance imaging and various diagnostic and interventional applications associated therewith.

BACKGROUND

Magnetic resonance imaging (MRI), or nuclear magnetic resonance imaging, is a noninvasive imaging technique that uses the interaction between radio frequency pulses, a strong magnetic field (modified with weak gradient fields applied across it to localize and encode or decode phases and frequencies) and body tissue to obtain projections, spectral signals, and images of planes or volumes from within a patient's body. Magnetic resonance imaging is particularly helpful in the imaging of soft tissues and may be used for the diagnosis of disease. Real-time or cine MRI may be used for the diagnosis of medical conditions requiring the imaging of moving structures within a patient. Real-time MRI may also be used in conjunction with interventional procedures, such as radiation therapy or image guided surgery, and also in planning for such procedures.

SUMMARY

Magnetic resonance imaging systems, methods and software are disclosed. Some implementations may be used in conjunction with a main magnet having a low field strength, a gradient coil assembly, an RF coil system, and a control system configured for the acquisition and processing of magnetic resonance imaging data from a human patient while utilizing a sparse sampling imaging technique without parallel imaging.

In some variations, the field strength of the main magnet is less than 1.0 Tesla and in others the field strength is approximately 0.35 T.

In some implementations, the control system of the MRI may be configured to utilize low gradient field strengths (e.g., below 20 mT/m), to utilize large flip angles (e.g., greater than 40 degrees), to utilize RF bandwidths to maintain chemical shift and magnetic susceptibility artifacts to less than one millimeter (e.g., RF bandwidths less than 1800 Hz), to utilize a gradient slew rate above 75 mT/m/ms, and/or to employ pulse sequences that do not require dephasing or spoiler pulses. In some implementations, the RF coil system may not include a surface coil.

The control system of the magnetic resonance imaging system may also be configured to produce cine MRI (e.g., of at least 4 frames per second).

In another implementation, the magnetic resonance imaging system may be integrated with a radiation therapy device for radiation treatment of a human patient and the control system may be further configured to utilize cine MRI to track the locations of tissues in the human patient. The radiation therapy device may be a linear accelerator having an energy in the range of, for example, 4-6 MV. The radiation therapy device may also be a proton therapy system, heavy ion therapy system, or a radioisotope therapy system.

The magnetic resonance imaging system may also comprise a split/open bore magnet and be configured to allow for surgical intervention in the gap of the split magnet, for example, with a robotic surgical device integrated into the system. Similarly, the gradient coil assembly may be a split gradient coil assembly. The main magnet may be a superconducting magnet, a non-superconducting magnet, or a resistive magnet. The main magnet may be powered by a battery system.

Implementations of the current subject matter can include, but are not limited to, methods consistent with the descriptions provided herein as well as articles and computer program products that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

The present disclosure describes systems, methods and computer software allowing for, among other things, high-quality magnetic resonance imaging with limited magnetic susceptibility distortions and chemical shift artifacts resulting in submillimeter spatial accuracy, high frame rate cine capability with an appropriate specific absorption rate (SAR), and the ability to support real-time 2-D and volumetric MRI-guided diagnostic and interventional applications.

Figure 1:
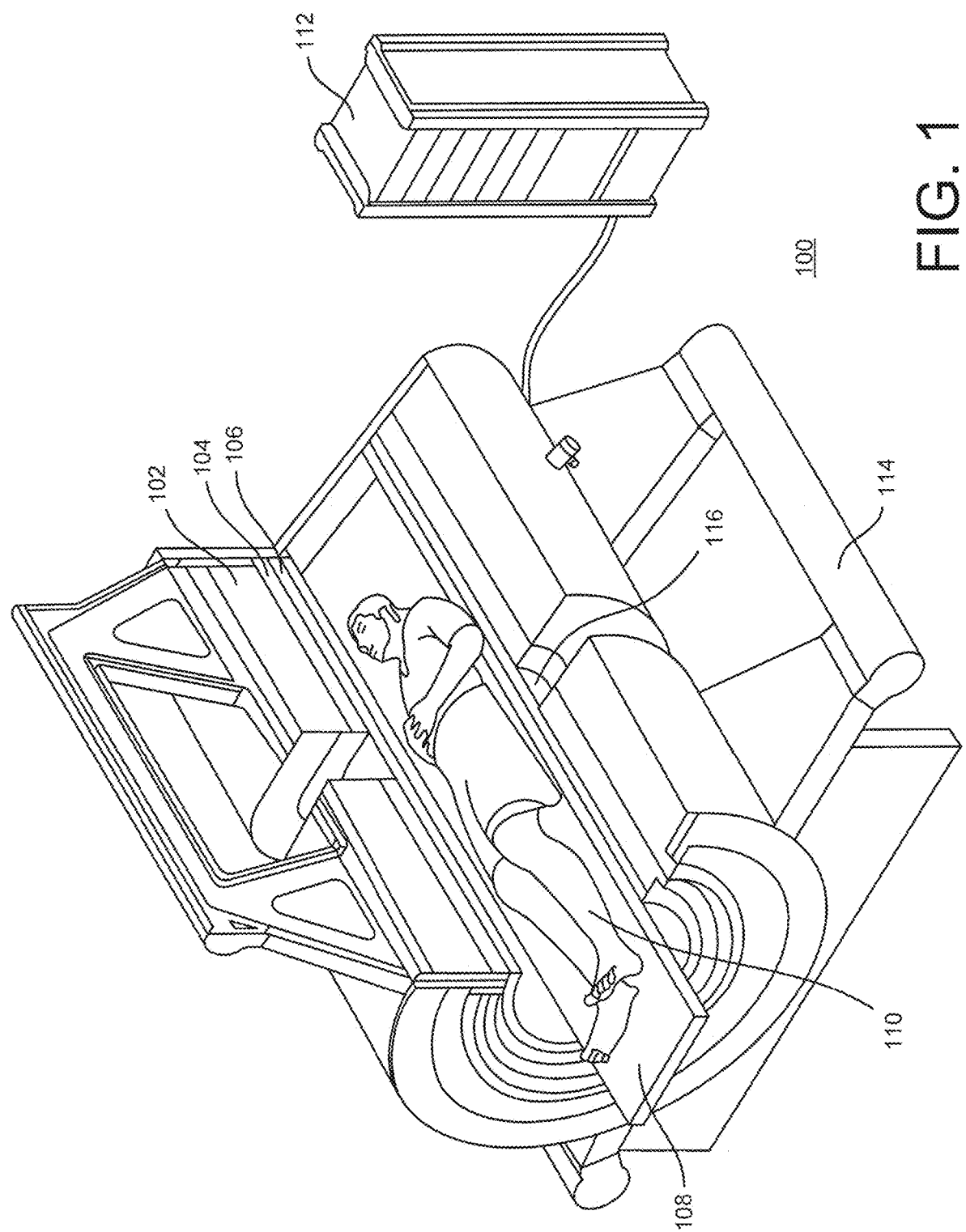
FIG. 1 is a diagram illustrating a simplified perspective view of an exemplary magnetic resonance imaging system in accordance with certain aspects of the present disclosure.

FIG. 1 illustrates one implementation of a magnetic resonance imaging system (MRI) 100 consistent with certain aspects of the present disclosure. In FIG. 1, the MRI 100 includes a main magnet 102, a gradient coil assembly 104 and an RF coil system 106. Within MRI 100 is a patient couch 108 on which a human patient 110 may lie. MRI 100 also includes a control system 112, discussed in detail below.

The main magnet 102 of MRI 100 may be a cylindrical split or open bore magnet separated by buttresses 114, with a gap 116 as shown in FIG. 1, a closed-bore cylindrical configuration, a C-shaped configuration, a dipolar magnet, or the like. Main magnet 102 may be comprised of a number of magnet types, including electromagnets, permanent magnets, superconducting magnets, or combinations thereof. For example, one combination or "hybrid" magnet may include permanent magnets and electromagnets. Main magnet 102 may be configured for any commonly used field strength, but is preferably configured for a low field strength. When the term low field strength is used herein, it refers to a field strength of less than 1.0 Tesla. In particular implementations of the present disclosure, the field strength of main magnet 102 may be configured to be in the range of 0.1 to 0.5 Tesla, or configured to be approximately 0.35 Tesla. The system may be designed to use resistive or permanent magnets, or a combination thereof, for example, when the field strength of the main magnet is less than approximately 0.2 Tesla. In one implementation, a system utilizing resistive magnet(s) may be powered by a direct-current battery system, for example, a lithium ion system such as, or similar to, a Tesla Powerwall.

Gradient coil assembly 104 contains the coils necessary to add small varying magnetic fields on top of main magnet 102's field to allow for spatial encoding of the imaging data. Gradient coil assembly 104 may be a continuous cylindrical assembly, a split gradient coil assembly as shown in FIG. 1, or other designs as may be necessary for the particular MRI configuration utilized.

RF coil system 106 is responsible for exciting the spins of hydrogen protons within patient 110 and for receiving subsequent signals emitted from patient 110. RF coil system 106 thus includes an RF transmitter portion and an RF receive portion. The implementation in FIG. 1 includes a singular body coil performing both the RF transmit and RF functionalities. RF coil system 106 may alternatively divide transmit and receive functionalities between a body coil and a surface coil, or may provide both transmit and receive functionalities within a surface coil. The RF coil system 106 depicted in the implementation of FIG. 1 has a continuous cylindrical form but could also be designed in a split manner, so that gap 116 would be open from the patient to the outer edge of main magnet 102.

Control system 112 is configured for the acquisition and processing of magnetic resonance imaging data from patient 110, including image reconstruction. Control system 112 may contain numerous subsystems, for example, those which control operation of the gradient coil assembly 104, the RF coil system 106, portions of those systems themselves, and those that process data received from RF coil system 106 and perform image reconstruction.

In one advantageous implementation, control system 112 is configured to utilize a sparse sampling imaging technique without parallel imaging. When the term sparse sampling imaging technique is used herein it refers to image acquisition and reconstruction techniques where only a portion of frequency space is measured (for the purposes of the present disclosure, 50% or less of the frequency information used to reconstruct an image using standard back-projection methods), and the image reconstruction is performed by optimization of the reconstructed image to be consistent with a priori knowledge of the imaged subject while also generally satisfying consistency between the frequency information of the reconstructed image and the measured frequency information. Sparse sampling imaging techniques thus include techniques such as compressed sensing and the volumetric imaging technique disclosed in U.S. Patent Application No. 62/353,530, filed concurrently herewith and assigned to ViewRay Technologies, Inc.

Parallel imaging techniques are commonly used in magnetic resonance imaging, especially with cine MRI, to shorten the time required for data acquisition. Parallel imaging methods use knowledge of the spatial distribution of signals received by multiple RF detectors (such as a surface coil having an array of these "elements") to replace some of the time-consuming phase-encoding steps in the MRI process. In this manner, signal is received from multiple coil elements "in parallel," and the sampling of fewer portions in k-space along readout trajectories (i.e., fewer phase encodings) is compensated for by the duplicity of data from all coil elements.

However, certain implementations of the present disclosure contemplate data acquisition and processing without utilizing parallel imaging techniques. In such cases where the present disclosure refers to magnetic resonance data acquisition and processing "without parallel imaging" it contemplates systems, methods and computer software designed to incorporate a small amount parallel imaging (perhaps in an attempt to avoid infringement), but not enough to create a perceptively significant increase in signal-to-noise ratio, all other things being constant.

In some advantageous implementations, the MRI and control system 112 may be configured to utilize low gradient field strengths, for example below 20 mT/m or, in other cases, below 12 mT/m. In addition, some advantageous implementations may utilize a relatively high gradient slew rate or rise time, such as a slew rate above 75 mT/m/ms. Control system 112 may also be advantageously configured to utilize large flip angles, for example, greater than 40 degrees. In addition, control system 112 may be advantageously configured to employ pulse sequences that do not require dephasing pulses (it is contemplated that such pulse sequences have no dephasing pulses, or have only a small number of dephasing or spoiling pulses such that there is no significant increase in data acquisition time from the standpoint of patient throughput).

In some implementations, control system 112 may be configured to utilize RF bandwidths to maintain chemical shift and magnetic susceptibility artifacts below one millimeter or even below one half of a millimeter. As an example, control system 112 may be configured for an RF bandwidth less than 1800 Hz. An evaluation of potential worst-case artifacts due to magnetic susceptibility and chemical shift can be evaluated. For example, for a worst case of, e.g., 8 ppm perturbation observed in human susceptibility assessments, formula [1] below can be used to estimate magnetic susceptibility artifacts.

$$\delta_{ms} \text{ [mm]} = mag. \text{ } suscept. \text{ [ppm]} \times \frac{B_o \text{ [T]}}{G_e \text{ [T/mm]}} \quad [1]$$

Here $\delta_{ms}$[mm] is the spatial distortion in millimeters due to magnetic susceptibility artifacts due to a magnetic susceptibility induced magnetic field change, mag. suscept. [ppm] in parts per million of the main magnetic field strength, $B_o$[T], in Tesla, and where $G_e$[T/mm] is the gradient encoding strength in Tesla per millimeter.

And, formula [2] below may be used to estimate displacements due to chemical shift.

$$\delta_{cs} \text{ [mm]} = 3.5 \text{ [ppm]} \times PixelSize \text{ [mm]} \times \frac{f_{B_o} \text{ [Hz]}}{BW \text{ [Hz/pixel]}} \quad [2]$$

Here $\delta_{cs}$[mm] is the spatial distortion in millimeters due to chemical shift artifacts, where 3.5 [ppm] is the relative parts per million difference in the Larmour frequency for Hydrogen bound to Oxygen (H—O) versus Carbon (C—H) for a Pixel or Voxel size, PixelSize, in millimeters, and $f_{B_o}$ is the Larmour frequency for Hydrogen in water and BW[Hz/pixel] is the frequency bandwidth for a pixel or voxel in Hertz per pixel or voxel.

A worst-case distortion can be taken as the sum of these two distortions plus any residual distortions due to uncorrected gradient field nonlinearities.

In one particular implementation of the magnetic resonance imaging system 100 of the present disclosure, the main magnet 102 field strength is approximately 0.35 Tesla and control system 112 is configured to utilize gradient field strengths below 12 mT/m, a gradient slew rate above 75 mT/m/ms, flip angles greater than 40 degrees, RF bandwidths less than 1800 Hz and pulse sequences that do not contain dephasing pulses. Control system 112 may also be configured to utilize a sparse sampling imaging technique without parallel imaging.

In another implementation of magnetic resonance imaging system 100, the main magnet 102 field strength is approximately 0.15 Tesla and control system 112 is configured to utilize gradient field strengths below 10 mT/m, a gradient slew rate above 75 mT/m/ms, flip angles greater than 60 degrees, RF bandwidths less than 1000 Hz and pulse sequences that do not contain dephasing pulses. In this implementation, control system 112 may also be configured to utilize a sparse sampling imaging technique without parallel imaging.

As discussed further herein, certain implementations of the systems, methods and computer software of present disclosure can be beneficial for cine planar, cine multi-planar, or real time volumetric or "4-D" (3-D spatial plus the time dimension) magnetic resonance imaging. Control system 112 may thus be configured to acquire and process data as necessary to reconstruct images to create cine MRI, for example, enabling cine MRI of at least 4 frames per second while maintaining an acceptable specific absorption rate in patient 110.

Conventional wisdom is that a high main magnet field strength is always preferred due to higher signal-to-noise ratio, with the desired field strength being limited mainly by size and cost considerations. Through higher signal-to-noise, contrast, and resolution, a higher field strength typically facilitates an improved ability for physicians to make diagnoses based on the resulting images. Yet, implementations of the present disclosure utilizing low main magnet field strengths (e.g., below 1.0 Tesla) result in high quality images and provide a number of additional benefits.

For example, implementations of the present disclosure can include RF bandwidths less than 1800 Hz, resulting in increased chemical shift artifacts (i.e., where hydrogen atoms in different chemical environments such as water and fat are partially shielded from the main magnetic field due to the difference in sharing of electrons involved in O—H and C—H chemical bonds, and hence have different nuclear magnetic resonance chemical shifts, appearing in different spatial locations when locating signals with frequency encoding). While high field systems will exhibit significant chemical shift artifacts, and require higher RF bandwidths (and their accompanying lower signal-to-noise ratios), the low field systems disclosed herein can use lower RF bandwidths and maintain high spatial integrity.

In addition, high main magnetic field strength systems will exhibit significant magnetic susceptibility artifacts where the diamagnetic and paramagnetic (and in rare cases ferromagnetic) nature of the imaged subject perturbs the magnetic field, leading to spatially distorted images. Such issues in higher field systems might typically be addressed through an increase in gradient field strengths, but implementations of the present disclosure avoid the same level of artifacts and thus may utilize lower gradient field strengths, resulting in improved signal-to-noise ratio and a lower specific absorption rate.

Moreover, the systems, methods and software discussed herein can be implemented without parallel imaging, which would cause a decrease in the signal-to-noise ratio of the resulting images that would increase with the speed of the imaging. Instead, the sparse sampling techniques disclosed herein allow for high frame rate acquisition with a relatively high signal-to-noise ratio that does not significantly decrease with image acquisition speed, for example, through the use of a priori data acquired before scanning, avoiding the use of "gridded" k-space data, and applying iterative optimization techniques. The use of phased array receive coils may also be avoided in the absence of parallel imaging, thereby achieving high quality imaging with less complex technology. Fewer RF receive channels may be used, in fact, only a single RF receive channel may be employed, along with a less expensive spectrometer.

Certain implementations of the present disclosure can also be employed without surface coils in contact with the patient. Instead, imaging may be performed with merely a body coil integrated into the bore of the MRI that contains both the transmit and receive coils.

In addition, simultaneous multiple slice imaging techniques may be beneficially employed, where multiple imaging slices or sub-volumes may be simultaneously excited and simultaneously read out. One implementation of simultaneous multiple slice excitation can sum multiple RF waveforms with different phase modulation functions resulting in a multiband pulse that can excite desired slices in the presence of a common slice selective gradient.

Furthermore, implementations of the present disclosure may utilize relatively high flip angles, which, at higher main magnet field strengths, would cause excessive patient heating. The higher flip angles in implementations of the present disclosure will result in improved image contrast and signal-to-noise ratios.

Additionally, the low main magnet field strength implementations discussed herein will exhibit faster RF signal decay, allowing for pulse sequences that do not require dephasing pulses (with the attendant advantage of a lower specific absorption rate).

The low main magnet field strength of certain implementations of the present disclosure also allows for lower frequency RF excitation pulses and thus decreased heating of the patient tissues by those pulses.

Further still, the well-controlled specific absorption rates exhibited by implementations of the present disclosure provide the ability to acquire and process data at a speed sufficient for high frame rate cine MRI.

With the numerous above described advantages, implementations of the present disclosure are well-suited for high quality cine MRI having an acceptable patient specific absorption rate. These implementations also control magnetic susceptibility and chemical shift artifacts so as to provide high spatial integrity, which can be critical in certain diagnostic and interventional applications.

Implementations of the present disclosure can be beneficial in numerous applications for diagnostic cine MRI, examples include anatomic localizers, repeated rapid imaging for localization and the study of movement (e.g., phonation), imaging freely moving subjects (e.g., fetal MRI), cardiac imaging, and the like.

Implementations of the present disclosure can also be beneficial in interventional applications, which also benefit from the advantages of high spatial integrity and controlled specific absorption rate. Examples of interventional applications include angioplasty, stent delivery, thrombolysis, aneurysm repair, vertebroplasty, fibroid embolization, and many other applications where fluoroscopy is currently used (and where the use of cine MRI will decrease radiation dose to the patient).

Implementations of the present disclosure may also be used for image guided surgery, and may provide real-time intraprocedural guidance in multiple orthogonal planes, imaging feedback regarding instrument position, guidance and/or warning systems and the like. An open bore MRI implementation, similar to that depicted in FIG. 1 (but with a split RF coil system 106) can be particularly beneficial for such interventional procedures. MRI 100 may thus be configured to allow for surgical intervention in the gap of a split magnet and may further include a robotic surgical device integrated with the system.

Yet another advantage of the low field strength attendant to certain implementations of the present disclosure is the decreased magnetic forces that will be exerted on any interventional equipment employed in conjunction with MRI 100 such as robotic surgery equipment, biopsy instrumentation, cryogenic ablation units, brachytherapy equipment, radiation therapy equipment, and the like.

In one implementation of magnetic resonance imaging system 100, in combination with interventional equipment (e.g., radiation therapy equipment such as a linac), a low field strength, non-superconducting magnet is utilized, for example, a resistive magnet, a permanent magnet, or hybrid magnet.

Another beneficial application of certain implementations of the present disclosure is in the field of image guided radiotherapy. Radiotherapy applications will also benefit from the present disclosure's ability to provide high frame rate cine MRI with high spatial integrity, both of which are key to accurately tracking a target being treated and to avoid hitting patient critical structures with significant amounts of ionizing radiation.

Figure 2:
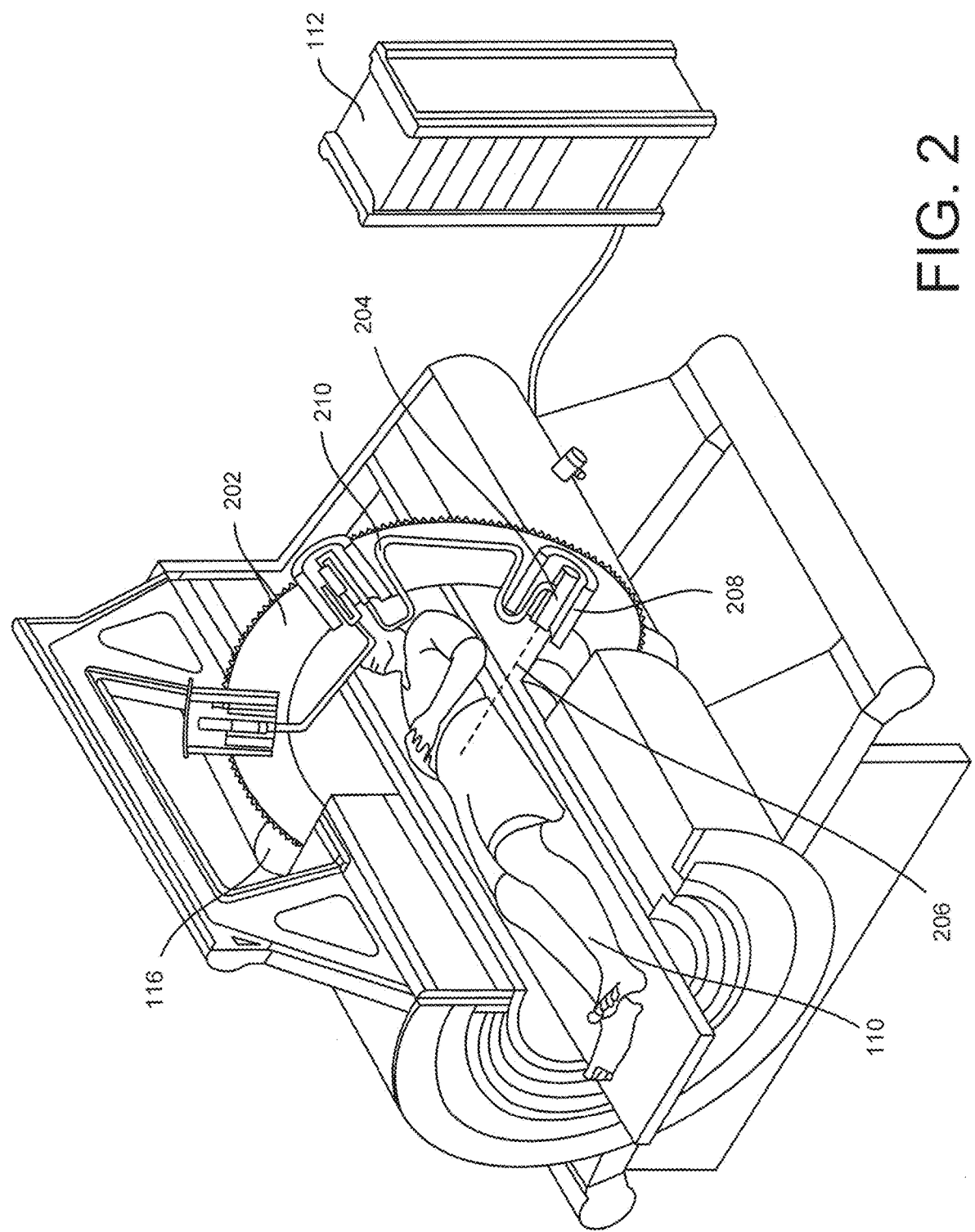
FIG. 2 is a diagram illustrating a simplified perspective view of an exemplary magnetic resonance imaging system incorporating an exemplary interventional device in accordance with certain aspects of the present disclosure.

FIG. 2 illustrates MRI 100 further configured to integrate a radiation therapy device to treat patient 110. In one implementation, MRI 100 may include a gantry 202 positioned in gap 116 of an open bore MRI. Gantry 202 can incorporate radiation therapy device 204, configured to direct a radiation therapy beam 206 toward patient 110. In one particular implementation, radiation therapy device 204 may be a linear accelerator having an energy in the range of 4-6 MV and, as depicted, the components of the linear accelerator may be divided into separate shielding containers 208 spaced about gantry 202. These linac components may then be connected by RF waveguides 210. While FIG. 2 depicts a particular radiation therapy device arrangement, the present disclosure contemplates the integration of any type of radiation therapy system such as proton therapy, heavy ion therapy, radioisotope therapy, etc.

As noted above, control system 112 of magnetic resonance imaging system 100 may be configured for cine MRI and further configured to utilize cine MRI to track the locations of tissues in the human patient 110.

An additional benefit of implementations of the present disclosure utilizing a main magnet 102 with a low field strength is a decrease in distortions of the delivered ionizing radiation dose distribution in patient 110 caused by the magnetic Lorenz force acting on the transport of secondary electrons (and positrons). The Lorenz force exerted by a higher field main magnet would overpower the scattering power of the electrons (and positrons), and cause them to spiral off their natural course, trapping them at low density interfaces—potentially resulting in unintended and harmful dose concentrations in the patient.

Figure 3:
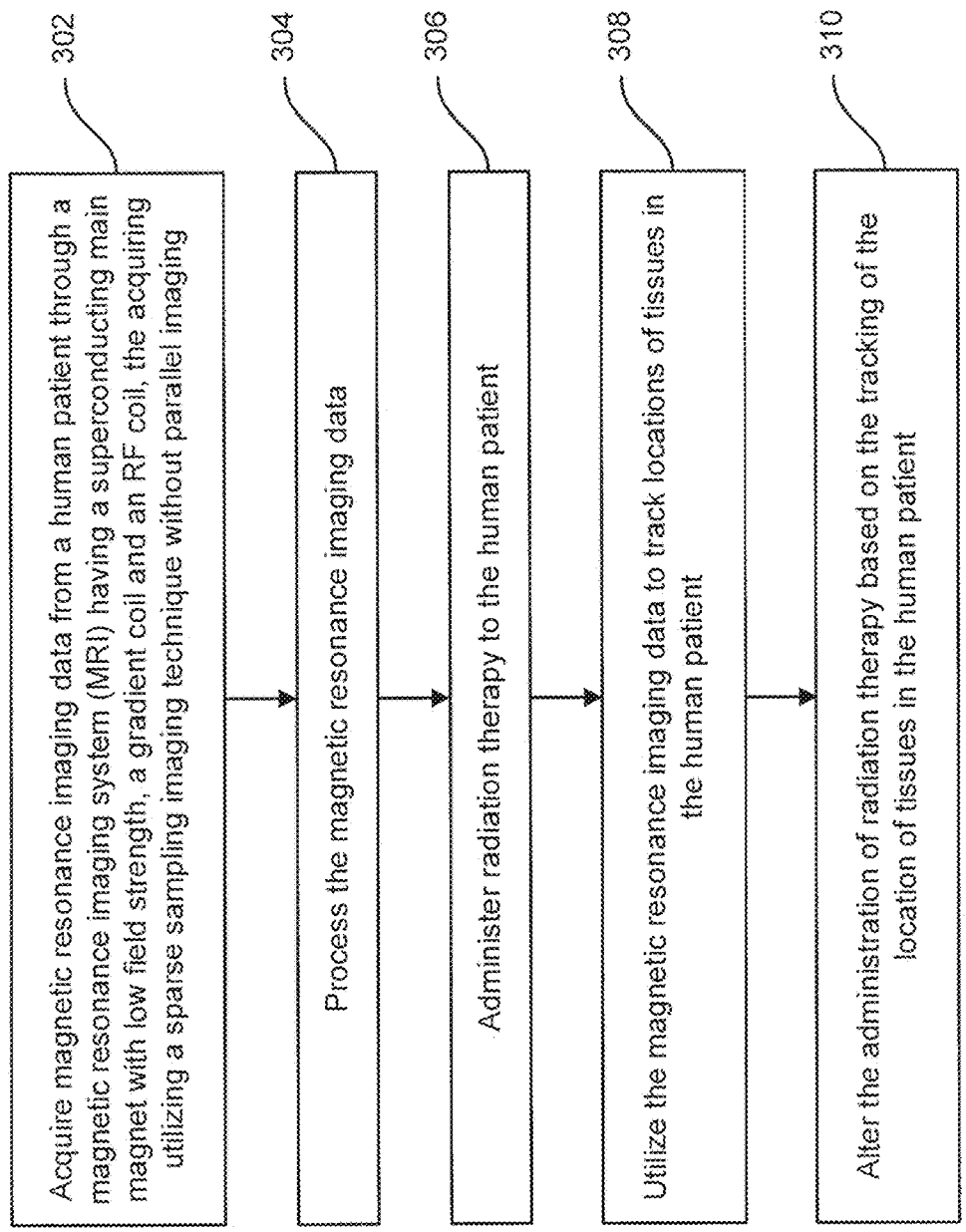
FIG. 3 is a simplified diagram for an exemplary method of real-time MRI-guided radiation therapy in accordance with certain aspects of the present disclosure.

An exemplary method for real-time image guided radiotherapy, consistent with implementations of the present disclosure, is illustrated in FIG. 3. At 302, magnetic resonance imaging data may be acquired from a human patient 110 through magnetic resonance imaging system 100 having a superconducting main magnet with low field strength, a gradient coil assembly 104, and an RF coil system 106, where the acquisition utilizes a sparse sampling imaging technique without parallel imaging. At 304, the magnetic resonance imaging data is processed. At 306, radiation therapy is administered to human patient 110. At 308, the magnetic resonance imaging data is utilized to track the locations of tissue(s) in the patient 110. And, at 310, the administration of radiation therapy may be altered based on the tracking of the location of tissue(s) in patient 110. In altering therapy, actions such as stopping the therapy, reoptimizing the therapy, adjusting the radiation therapy beam and the like are contemplated. The exemplary method illustrated in FIG. 3 may also incorporate any or all of the characteristics described above (e.g., low gradient field strengths, large flip angles, RF bandwidths to maintain spatial integrity, particular pulse sequences, etc.).

When the present disclosure indicates that the magnetic resonance imaging system is configured to operate in a particular manner, it means that such system is setup and intended to be operated in that manner, regardless of whether it may also be configured to utilize pulse sequence(s) or configurations that do not operate in the manner described or claimed herein.

The present disclosure contemplates that the calculations disclosed in the embodiments herein may be performed in a number of ways, applying the same concepts taught herein, and that such calculations are equivalent to the embodiments disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Specifically, and by way of example, although the headings refer to a "Technical Field," such claims should not be limited by the language chosen under this heading to describe the so-called technical field. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A magnetic resonance imaging system (MRI) comprising:
   a main magnet having a field strength less than 1.0 Tesla;
   a gradient coil assembly;
   an RF coil system; and
   a control system configured for acquisition and processing of magnetic resonance imaging data from a human patient and configured to utilize a sparse sampling imaging technique without parallel imaging and to employ simultaneous multiple slice imaging techniques.

2. The magnetic resonance imaging system of claim 1, wherein the multiple slice imaging techniques comprise simultaneously exciting and simultaneously reading out a plurality of imaging slices or sub-volumes.

3. The magnetic resonance imaging system of claim 2, the control system configured to generate a common slice selective gradient and to generate a multiband pulse to excite the plurality of imaging slices or sub-volumes in the presence of the common slice selective gradient.

4. The magnetic resonance imaging system of claim 1, the multiple slice imaging techniques comprising generating a multiband pulse by summing multiple RF waveforms with different phase modulation functions.

5. The magnetic resonance imaging system of claim 1, wherein the control system is further configured for an RF bandwidth to be less than 1800 Hz.

6. The magnetic resonance imaging system of claim 1 wherein the control system is configured to employ pulse sequences that do not require dephasing pulses.

7. A computer program product comprising a non-transient, machine-readable medium storing instructions which, when executed by at least one programmable processor, cause the at least one programmable processor to perform operations comprising:
   acquiring magnetic resonance imaging data from a human patient through a magnetic resonance imaging system (MRI) having a main magnet with low field strength, a gradient coil assembly and an RF coil system, the acquiring utilizing a sparse sampling imaging technique without parallel imaging and employing simultaneous multiple slice imaging techniques; and
   processing the magnetic resonance imaging data, the processing including reconstructing images of the human patient.

8. The computer program product of claim 7, the operations further comprising exciting and simultaneously reading out a plurality of imaging slices or sub-volumes.

9. The computer program product of claim 8, the operations further comprising:
   generating a common slice selective gradient; and
   generating a multiband pulse to excite the plurality of imaging slices or sub-volumes in the presence of the common slice selective gradient.

10. The computer program product of claim 7, the operations further comprising generating a multiband pulse by summing multiple RF waveforms with different phase modulation functions.

11. The computer program product of claim 7, wherein the control system is further configured for an RF bandwidth to be less than 1800 Hz.

12. The computer program product of claim 7, wherein the acquiring employs pulse sequences that do not require dephasing pulses.

* * * * *